United States Patent [19]

Grachev et al.

[11] 4,232,967
[45] Nov. 11, 1980

[54] INSTRUMENT FOR MEASURING SIZES AND QUANTITY OF PARTICLES IN FLUID MEDIUM

[76] Inventors: Konstantin A. Grachev, Naberezhnaya Kosmonavtov, 3, kv. 67; Viktor A. Berber, ulitsa Shelkovichnaya, 184, kv. 65; Viktor E. Sokolov, ploschad Ordzhonikidze, 14, kv. 17; Vladimir V. Pavlov, ulitsa Sovetskaya, 21, kv. 56; Alexei N. Popov, ulitsa Zheleznodorozhnaya, 5/9, kv. 31; Vladimir A. Zolotenko, 2 Detsky proezd, 2, kv. 18, all of Saratov, U.S.S.R.

[21] Appl. No.: 920,998

[22] Filed: Jun. 30, 1978

[51] Int. Cl.³ .......................................... G01N 15/02
[52] U.S. Cl. .................................. 356/336; 250/565; 250/574; 356/339; 356/341; 356/243
[58] Field of Search ............... 356/336, 339, 341, 243; 250/564, 565, 574

[56] References Cited

U.S. PATENT DOCUMENTS 3,127,464  3/1964  Gustavson ..................... 356/243 X
3,819,269  6/1974  Duvall et al. ................... 356/336 X

OTHER PUBLICATIONS

Kirsh et al., "Improvement and Calibration of an AZ Jet Type Photoelectric Aerosol Counter," *Kolloidnyi Zhurual*, vol. 37, No. 4, pp. 778–781, Jul.–Aug. 1975.

*Primary Examiner*—John K. Corbin
*Assistant Examiner*—Matthew W. Koren
*Attorney, Agent, or Firm*—Haseltine, Lake & Waters

[57] ABSTRACT

According to the invention, the instrument for measuring the sizes and quantity of particles in a fluid medium comprises a light-sensitive device which converts light scattered by particles in a flow of a fluid medium which crosses a beam emitted by a light source, as well as some part of the light of that beam, arriving from an element whose purpose is to simulate a calibrated particle, to electric pulses. The light-sensitive device is connected via a divider, whose purpose is to distribute pulses according to the sizes of particles, to signal inputs of respective threshold devices whose outputs are connected to inputs of counters with indicators. The element which simulates a calibrated particle is adapted to periodically change, in the course of measurement, the brightness of light received by the light-sensitive device. Interposed between the output of the light-sensitive device and reference inputs of the threshold devices is a circuit for converting output devices of the light-sensitive device to direct-current voltage which adjusts the trigger levels of the threshold devices according to the amplitude of a pulse arriving from the element which simulates a calibrated particle.

4 Claims, 4 Drawing Figures

INSTRUMENT FOR MEASURING SIZES AND QUANTITY OF PARTICLES IN FLUID MEDIUM

The present invention relates to instrument making and, more particularly, to instruments for measuring the sizes and quantity of particles in a fluid medium.

The most effective application of the instrument in accordance with the invention is the control of air pollution in shops and other production facilities.

The instrument of this invention can also be used to determine the degree of pollution of fluids in the chemical industry and at machine-building works.

The instrument according to the invention can further be used in medicine for analyzing the composition of blood and other fluids.

There are known instruments for measuring the sizes and quantity of particles in a fluid medium of the type that comprises a dark chamber, wherein a beam of light is emitted by a light source and shaped by a system of lenses. The chamber also accommodates a light-sensitive device which receives light scattered by particles found across the path of the light beam. The particles are introduced into the chamber with a flow of a fluid medium being investigated, which is directed transversely to the light beam. The light-sensitive device converts the flashes of light, scattered by the particles, to electric pulses. The output of the light-sensitive device is connected via a divider, whose purpose is to distribute pulses according to the sizes of particles, to signal inputs of threshold devices. Outputs of the threshold devices are connected to inputs of counters with indicators.

The accuracy of the instrument is checked with the aid of an element which simulates calibrated particles. This element comprises a movable member which is made to cross the light beam prior to measurement.

The accuracy of the instrument is checked with the aid of an element which simulates calibrated particles. This element comprises a movable member which is made to cross the light beam prior to measurement.

The instrument under review is checked only a short time before the measurement; it is adjusted by the operator, which is an unnecessary complication in the use of the instrument. In addition, the instrument under review does not make it possible to eliminate the effects of such sources of error as unstable voltage of the power source, which may rapidly vary in the course of measurements.

It is an object of the present invention to provide an instrument for measuring the sizes and the quantity of particles in a fluid medium, wherein the design of the element simulating a calibrated particle would make it possible to automatize the calibration of the instrument, while using the instrument to measure the sizes and quantities of particles.

It is another object of the invention to improve the accuracy of measuring particle sizes.

It is still another object of the invention to facilitate the use of the instrument.

The invention essentially consists in providing an instrument for measuring the sizes and quantity of particles in a fluid medium, wherein a light-sensitive device, which converts light scattered by particles in a flow of a fluid medium crossing a beam emitted by a light source, as well as some part of light of that beam, arriving from an element simulating a calibrated particle, to electric pulses, is connected via a divider, whose purpose is to distribute these pulses according to particle sizes, to signal inputs of respective threshold devices whose outputs are connected to inputs of counters with indicators, the instrument being characterized, according to the invention, by that the element simulating a calibrated particle is adapted to periodically change, in the course of measurements, the brightness of part of the light received by the light-sensitive device, and by that interposed between the output of the light-sensitive device and reference inputs of the threshold devices is a circuit for converting output pulses of the light-sensitive device to d.c. voltage which adjusts the trigger levels of the threshold devices according to the amplitude of a pulse arriving from the element which simulates a calibrated particle.

It is expedient that the element simulating a calibrated particle should be shaped as a rod adapted for reciprocating motion so as to periodically enter the light beam, for which purpose the rod is coupled to an electromagnet's armature.

Such a design of the element simulating a calibrated particle is the simplest and accounts for a maximum accuracy of measurements.

The element simulating a calibrated particle may be designed as a light channel to transmit part of light of the beam emitted by the light source to the light-sensitive device, which channel accommodates a light chopper controlled by a drive.

The latter design makes it possible to adjust the brightness of light and, consequently, an equivalent calibrated particle size.

The instrument for measuring the sizes and quantity of particles in a fluid medium according to the invention is calibrated automatically in the course of measurements, which accounts for an excellent stability of the metrological characteristics of the instrument and a high accuracy of measurements.

Other objects and advantages of the present invention will become more apparent from the following detailed description of a preferred embodiment thereof to be read in conjunction with the accompanying drawings, wherein.

Figure 1:
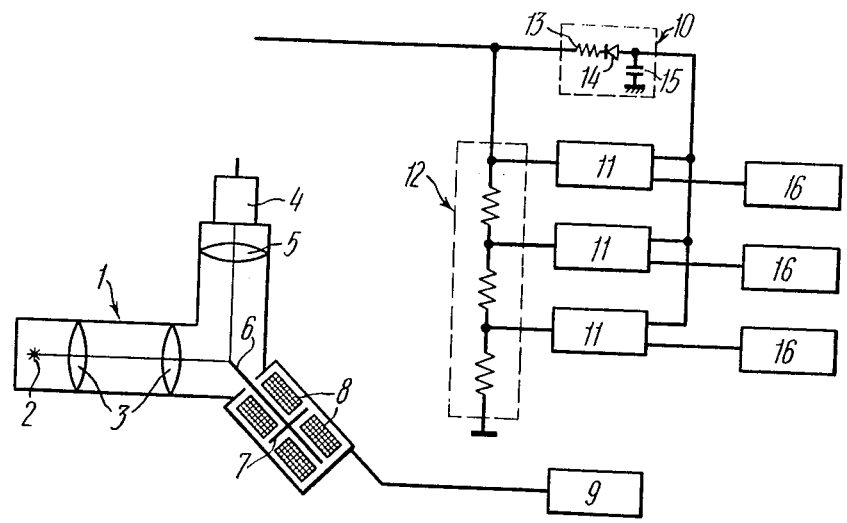
FIG. 1 is a schematic diagram of an instrument for measuring the sizes and quantity of particles in a fluid medium, in accordance with the invention, including an elevation view of an element for simulating a calibrated particle, which element is designed as a rod.

The invention will be further described in greater detail with reference to an instrument used to control air pollution. The instrument comprises a dark chamber 1 (FIG. 1) which accommodates a lamp 2 serving as a light source, and a system of lenses 3 intended for shaping a light beam. The chamber 1 further accommodates a light-sensitive device 4 whose visual ray, shaped by a system of lenses 5, extends at a perpendicular to the light beam produced by the source 2.

In order to introduce air to be checked for pollution into the chamber 1, the latter is provided with a nozzle (not shown) installed so as to direct the air flow at the point of intersection of the above-mentioned beams. An element 6 is intended to simulate a calibrated particle and is designed as a rod, also designated as 6, which is adapted to periodically change, in the course of measurements, the brightness of light received by the light-sensitive device 4.

In order to vary the brightness of light, the rod 6 is made movable so as to be able to enter the beam emitted by the light source 2; for this purpose, the rod 6 is coupled to an armature 7 of an electromagnet 8 supplied by a generator 9 which is solely meant to energize the electromagnet 8. The rod 6 is arranged so that while in motion, it periodically gets into the beam emitted by the light source 2, scattering some light of that beam in the direction of the light-sensitive device 4.

The light-sensitive device 4 serves to convert light it receives to electric pulses. Its function may be performed by any suitable light-sensitive device, for example, a photoelectronic multiplier. An output of the light-sensitive device 4 is connected to an input of a circuit 10 intended to convert output pulses of the light-sensitive device 4 to d.c. voltage; the output of the device 4 is also connected to signal inputs of threshold devices 11, which connection is effected via a divider 12 serving to distribute output pulses of the light-sensitive device 4 among the threshold devices 11 according to the sizes of particles contained in the air flow.

An output of the converter circuit 10 is connected to reference inputs of the threshold devices 11.

The circuit 10 for converting output pulses of the light-sensitive device 4 to d.c. voltage is an integrating circuit comprising a resistor 13, a diode 14 and a capacitor 15; the time constant of the integrating circuit is selected to be much longer than the duration of the pulse produced at the output of the light-sensitive device 4 as it receives light scattered by particles contained in the air flow; at the same time the time constant of the integrating circuit is less than the duration of the pulse produced at the output of the light-sensitive device 4 as it receives light scattered by the rod 6 which serves to simulate a calibrated particle. From the outputs of the threshold devices 11, pulses are applied to inputs of respective counters 16 with indicators intended to count and display the number of pulses corresponding to that of particles of each size group contained in the air being investigated.

The divider, threshold devices and counters with indicators may employ any known circuitries suitable to perform their respective functions.

The element for simulating a calibrated frequency may also be designed as a light-transmitting channel 17 (FIG. 2) comprising a system of mirrors 17a and accommodating a light chopper whose function is performed by a rod 6a coupled to the armature 7 of the electromagnet 8 as described above. Part of light is removed from the beam produced by the light source 2 (FIG. 1) by a diaphragm 18 put across the path of that beam.

The element simulating a calibrated frequency may further be designed as a light-transmitting channel 19 (FIG. 3) comprising a system of prisms 20 and accommodating a light chopper 21 controlled by an independent drive 22. The light chopper may be of any known type suitable for the purpose. Part of light is removed from the beam emitted by the light source 2 by a diaphragm 23 arranged across the path of that beam.

Figure 3:
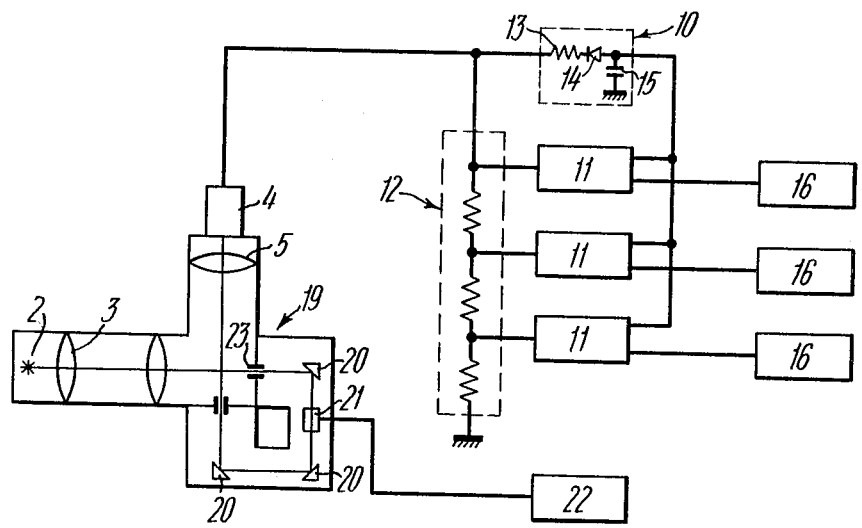
FIG. 3 is a schematic diagram of an instrument for measuring the sizes and quantity of particles in a fluid medium, according to the invention, wherein the element simulating a calibrated particle is designed as a system of prisms with a light chopper.
Figure 4:
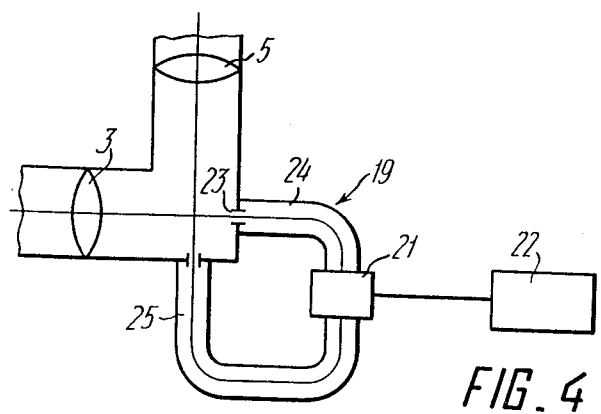
FIG. 4 is a view of a chamber accommodating light guides.

The light-transmitting channel 19 of FIG. 4 is composed of two light guides 24 and 25; interposed between the light guides 24 and 25 is a light chopper 21 similar to the one installed in the channel 19 of FIG. 3. Part of the beam's light is removed by a diaphragm 23 (FIG. 4).

The instrument for measuring the sizes and quantity of particles in a fluid medium operates as follows.

The light source 2 (FIG. 1) produces, and the system of lenses 3 shapes, a sharply defined narrow beam of light in the chamber 1. The flow of air to be checked for pollution, and particles contained therein, are directed through the nozzle, arranged at a perpendicular to the plane of the attached drawings, so that the air flow crosses the light beam. As a particle is caught in the light beam, it scatters a part of the beam's light in all directions; part of the light scattered by the particle gets into the visual ray of the light-sensitive device 4, shaped by the system of lenses 5. The light-sensitive device 4 converts the light it receives to electric pulses. The amplitudes of these pulses depend upon the brightness of light scattered by particles. From the output of the light-sensitive device 4, the pulses are applied via the ohmic divider 12 to the signal inputs of the threshold devices 11 which are thus excited for a period of time equal to the duration of the pulses. The number of threshold devices thus excited is determined by the pulse amplitude and, consequently, by the size of the particle which causes a pulse to appear. The pulse produced by the top-order (with respect to the pulse amplitude) threshold device of the excited threshold devices is applied to the input of the respective counter 16 with indicators intended to count and display the quantity of particles whose sizes are within the range of the given channel. Thus the size of a particle is derived from the amplitude of the pulse at the output of the light-sensitive device 4. The amplitude of a pulse at the output of the light-sensitive device 4 is determined by the size of a particle, as well as by a number of factors, including the brightness of the light source, the conversion coefficient of the light-sensitive device 4, the sensitivity of the threshold devices 11, etc.

In order to rule out the effects of these factors, the size of a particle is measured by comparing the amount of light scattered by the particle with the amount of light produced by the element which simulates a calibrated particle. A calibrated particle is simulated with the aid of the rod 6 which periodically gets into the light beam produced by the light source 2. The reflecting surface of the rod 6 and the depth of its penetration into the light beam are selected so as to ensure a constant intensity of the light scattered by the rod 6. The rod 6 is driven by the electromagnet 8 energized by the independent generator 9. The oscillation period of the generator 9 is to ensure that the duration of the pulse produced at the output of the light-sensitive device 4 by the light scattered by the rod 6 is much greater than the duration of the pulse caused to appear by a particle. All the pulses produced at the output of the light-sensitive device 4 are applied to the circuit 10 for converting output pulses of the light-sensitive device 4 to d.c. voltage.

The duration of pulses produced by particles contained in the air flow is significantly shorter than the time constant of the integrating circuit incorporated in the converter circuit 10; the number of particles producing pulses of great amplitudes is negligible; as a result, the pulses produced by particles contained in the air flow have no tangible effect upon the d.c. voltage across the output of the converter circuit 10. The duration of a pulse produced by the rod 6 is enough to bring the charge of the capacitor 15 to a level corresponding to the full amplitude of that pulse. As a result, at the output of the converter circuit 10 there is produced d.c. voltage whose level is equal to the amplitude of the pulse produced by the element simulating a calibrated particle. From the output of the converter circuit 10, d.c. voltage is applied to the reference inputs of the threshold devices 11. Of all the threshold devices 11, only that device is excited to whose signal input there is applied a pulse with an amplitude higher than the level of d.c. voltage at its reference input. Thus a change in the brightness of the light source 2, the conversion coefficient of the light-sensitive device 4 and other factors which affect the amplitudes of pulses produced by particles contained in the air flow is accompanied by a change in the amplitudes of pulses produced by particles contained in the air flow and in the level of d.c. voltage of the element which simulates a calibrated particle. To summarize, the sizes of particles contained in the air flow are measured by comparing these sizes with that of a calibrated particle, which is done right in the course of measurement and accounts for a substantial improvement in the accuracy of measurements.

In cases when the element simulating a calibrated particle is the light-transmitting channel 17 (FIG. 2) which transmits some light of the beam produced by the light source 2 to the light-sensitive device 4, a calibrated particle is simulated as follows.

The light beam, emitted by the light source 2 and shaped by the system of lenses 3, passes through the diaphragm 18 to reach the system composed of two mirrors 17a.

Figure 2:
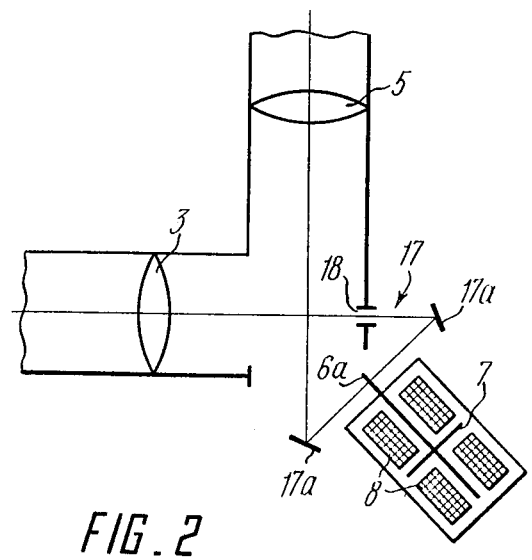
FIG. 2 is a view of a chamber with a system of mirrors, in accordance with the invention.

The light is refracted by the mirrors 17a, and part of the beam, which passes through the diaphragm 18, is directed at the light-sensitive device 4. Interposed between the mirrors 17a, across the path of the refracted beam, is the rod 6a which periodically chops the beam. In all other respects, the instrument operates as in the case when the function of the element simulating a calibrated particle is performed by the rod 6 (FIG. 1).

When the flexible light guides 24 and 25 (FIG. 4) are used to make up the light-transmitting channel 19, a calibrated particle is simulated as in the case of using the mirrors 17a and the system of prisms 20 in the light-transmitting channels 17 and 19. The function of the light chopper 21 is performed by half of a disc rotated by the independent drive 22.

What is claimed is:

1. An instrument for measuring the size and quantity of particles in a fluid medium, comprising a dark chamber; a light source accommodated within said chamber; means for shaping a light beam emitted by said light source received in said chamber; means for introducing the fluid medium into said chamber so that it crosses the light beam shaped from the light source; an element simulating a calibrated particle mounted within said chamber; a light-sensitive device installed in said chamber to convert the light scattered by particles contained in the flow of the fluid medium which crosses the shaped light beam emitted by said light source, and also a part of the light beam, directed from said element to electric pulses; said element for simulating a calibrated particle being adapted to periodic change, in the course of measurements, the brightness of the light received by said light-sensitive device; means for varying the brightness of the part of light received by said light-sensitive device; a converter circuit for converting output electric pulses of said light-sensitive device to d.c. voltage, the input of said circuit being connected to the output of said light-sensitive device; a divider having an input connected to the output of said light-sensitive device; threshold devices having their signal inputs connected to the outputs of said divider which serves to distribute the electric pulses received from light-sensitive device according to the size of particles to said threshold devices; the output of said converter circuit being connected to reference inputs of said threshold devices whose trigger levels depend on the d.c. voltage at the output of said converter circuit; means for counting and displaying the quantity of pulses corresponding to the number of particles in the flow being studied, separately for each size group.

2. An instrument as recited in claim 1, in which the element for simulating a calibrated particle is a rod adapted for reciprocating in order to be periodically introduced into the light beam, for which purpose said rod is coupled with an armature of an electromagnet.

3. An instrument as claimed in claim 1, wherein the element simulating a calibrated particle is a channel which transmits a part of the beam's light to the light-sensitive device, which channel accommodates a light chopper controlled by an independent drive.

4. The instrument as recited in claim 1, in which the element simulating a calibrated particle is a rod which being inserted periodically into the light flux at a point where it intersects the optical axis of the light sensing means to scatter some light of the beam in the direction of the light-sensitive device.

* * * * *